(12) United States Patent
Schwartz et al.

(10) Patent No.: US 8,106,041 B2
(45) Date of Patent: *Jan. 31, 2012

(54) COMBINATION PRODUCT COMPRISING AN ANTAGONIST OR INVERSE AGONIST OF HISTAMINE RECEPTOR H₃ AND AN ANTIPSYCHOTIC AND ANTIDEPRESSANT AGENT, AND USE THEREOF FOR THE PREPARATION OF A MEDICAMENT THAT PREVENTS THE ADVERSE EFFECTS OF PSYCHOTROPIC DRUGS

(75) Inventors: Jean-Charles Schwartz, Paris (FR); Jeanne-Marie Lecomte, Paris (FR)

(73) Assignee: Bioprojet, Paris (FR)

( * ) Notice: Subject to any disclaimer, the term of this patent is extended or adjusted under 35 U.S.C. 154(b) by 1213 days.

This patent is subject to a terminal disclaimer.

(21) Appl. No.: 10/562,396

(22) PCT Filed: Jun. 25, 2004

(86) PCT No.: PCT/FR2004/001628
§ 371 (c)(1),
(2), (4) Date: Apr. 14, 2006

(87) PCT Pub. No.: WO2005/000315
PCT Pub. Date: Jan. 6, 2005

(65) Prior Publication Data
US 2006/0210624 A1    Sep. 21, 2006

(30) Foreign Application Priority Data
Jun. 27, 2003 (FR) .................................. 03 07836

(51) Int. Cl.
*A61K 31/55* (2006.01)
*A61K 31/497* (2006.01)
*A01N 43/62* (2006.01)
*C07D 491/00* (2006.01)
*C07D 513/00* (2006.01)
*C07D 515/00* (2006.01)
*C07D 243/10* (2006.01)
*C07D 487/12* (2006.01)
*C07D 295/00* (2006.01)
*C07D 241/04* (2006.01)

(52) U.S. Cl. ............... 514/220; 514/252.12; 540/557; 544/398

(58) Field of Classification Search ................. 514/220, 514/252.12; 540/557; 544/398
See application file for complete search history.

(56) References Cited

U.S. PATENT DOCUMENTS
6,248,765 B1    6/2001  Schunack et al.
7,138,413 B1 *  11/2006 Schwartz et al. ............. 514/312
2002/0065278 A1  5/2002  Carruthers et al.
2003/0096808 A1  5/2003  Miller
2004/0220225 A1  11/2004 Schwartz et al.

FOREIGN PATENT DOCUMENTS
WO    WO 00/74784 A1 * 12/2000

OTHER PUBLICATIONS

Brittain, H.G., Polymorphism in Pharmaceutical Solids, 1999, Marcel Dekker Inc., pp. 1-2, 7, 185, 280-281, 321.*
Vohora D. et al; "Histamine and selective H3-receptor ligands: a possible role in the mechanism and management of epilepsy." Apr. 2001; pp. 735-741, vol. 68, No. 4; Pharmacology, Biochemistry, and Behavior; United States.
Stark H. et al; "Developments of Histamine H3-receptor Antagonists" 1996, pp. 507-520; vol. 21, No. 5, Drugs of the Future, Barcelona, Spain.
Monti J. M. et al; "Effects of selective activation or blockade of the histamine H3 receptor on sleep and wakefulness." Dec. 3, 1991, pp. 283-287; vol. 205, No. 3, European Journal of Pharmacology; Netherlands.
Miyazaki S. et al; "Effects of thioperamide, a histamine H3-receptor antagonist, on a scopolamine-induced learning deficit using an elevated plus-maze test in mice." 1995; pp. 2137-2144; vol. 57, No. 23; Life Sciences, England.
Ganellin C. R. et al; "synthesis of potent non-imidazole histamine H3-receptor antagonists" 1998; pp. 395-404; vol. 331, No. 12; Archiv Der Pharmazie; Germany.
Liedtke et al; "Replacement of imidazole by a piperidine moiety differentially affects the potency of histamine H3-receptor antagonists." Jan. 2003; pp. 43-50; vol. 367, No. 1; Naunyn-Schmiedeberg's Archives of Pharmacology; Germany. Meier et al; "Influence of imidazole replacement in different structural classes of histamine H3-receptor antagonists" Jun. 2001; pp. 249-259; vol. 13, No. 3; European Journal of Pharmaceutical Sciences.
Shadbolt et al; Some Aryloxyalkylamines, N-Arylethylenediamines and Related Compunds as Anorectic Agents 1971; pp. 836-842; vol. 14, No. 9; Journal of Medicinal Chemistry, American Chemical Society; Washington D.C.

* cited by examiner

*Primary Examiner* — Sreeni Padmanabhan
*Assistant Examiner* — Sarah Pihonak
(74) *Attorney, Agent, or Firm* — B. Aaron Schulman, Esq.; Terry L. Wright, Esq.; Stites & Harbison PLLC

(57) ABSTRACT

Medicament comprising, in a pharmaceutically acceptable vehicle, an anti-psychotic or an antidepressant (A), which, on its own, has an undesirable effect of a gain in body weight or sedation, and an antagonist and/or inverse agonist (B) of the histamine H₃ receptor, the antagonist and/or inverse agonist of the histamine H₃ receptor being present in a therapeutically effective amount for ensuring at least one of the following three effects: suppression or at least limitation of the undesirable effect of weight gain, suppression or limitation of the undesirable effect on alertness, epilepsy/convulsions, increase in the precognitive effect of the treatment. Use of such an antagonist or inverse agonist for the preparation of a medicament which is to ensure at least one of the said three effects in a patient treated by such an antipsychotic or antidepressant.

8 Claims, No Drawings

COMBINATION PRODUCT COMPRISING AN ANTAGONIST OR INVERSE AGONIST OF HISTAMINE RECEPTOR H₃ AND AN ANTIPSYCHOTIC AND ANTIDEPRESSANT AGENT, AND USE THEREOF FOR THE PREPARATION OF A MEDICAMENT THAT PREVENTS THE ADVERSE EFFECTS OF PSYCHOTROPIC DRUGS

The present invention relates to a new medicament constituted by a new combination for antipsychotic use or, more generally, psychotropic use.

A number of psychotropic agents administered chronically have the disadvantage of inducing in patients an excessive weight gain which is an extremely distressing effect.

This is particularly true of second-generation antipsychotics, which are currently the most commonly used agents in schizophrenia (Blackburn G. L., *J. Clin. Psych.* 2000, 61, 36; Bobes J. et al., *Schizophrenia Res.* 2003, 62, 77) but also concerns a number of antidepressants and other psychotropic agents (Ackerman S. and Nolom L. J., *CNS Drugs* 1998, 9, 135).

It is thus that continuous treatment with antipsychotic agents, such as olanzapine, risperidone, clozapine, quetiapine, or antidepressants, such as mirtazapine, amitriptyline or paroxetine, induces monthly weight gains of from 1 to 2.5 kg and total weight gains which may exceed 4 kg (Bobes et al., 2003). This undesirable effect occurs in up to approximately 50% of patients treated, in whom it is found to be extremely distressing, particularly in the case of women. It often leads to a reduction in the benefit of the treatment in the opinion of the patient, who reduces the doses thereof or even abandons it, which leads to relapses which become increasingly difficult to treat. In addition, it has been established that weight gains of that amplitude can significantly increase the risk of type 2 diabetes, cardiovascular disorders and cancer. Several attempts to prevent this undesirable effect by combining antipsychotics with agents such as fluoxetine (Bustillo J. R. et al. *Neuropsychopharmacol.* 2003, 28, 527), sibutramine (Heiman et al., *World J. Biol. Psycho.* 2001, 2, 2515), amantadine (Baptista et al., *Pharmacopsychiatry* 1997, 30, 43) or tamoxifen (Baptista et al., *Pharmacopsychiatry* 1997, 57, 215) have not been sufficiently convincing to be followed up by therapeutic application.

The mechanism by which this undesirable effect occurs is still in dispute because the majority of psychotropic agents interact with several brain receptors. In this respect, mention has been made in particular of the blocking of $5HT_{2A}$, $5HT_{2C}$, α-adrenergic or histaminergic $H_1$ receptors.

The object of the present invention is to overcome those disadvantages and to permit antipsychotic treatment or, more generally, psychotropic treatment by so-called second-generation neuroleptic antipsychotics, while avoiding or limiting the weight gain associated with the treatment and while preventing or delaying the occurrence of associated complications and, in particular, the risk of type 2 diabetes, cardiovascular disorders and/or neoplasic diseases.

Another object of the invention is to provide such a means of treatment which is substantially free from other secondary effects.

Yet another object of the invention is, in some cases, to improve the efficacy of antipsychotic treatment.

The present invention relates to a new medicament comprising, in a pharmaceutically acceptable vehicle, an antipsychotic or an antidepressant (A), which, on its own, has an undesirable effect of a gain in body weight or sedation, and an antagonist and/or inverse agonist (B) of the histamine $H_3$ receptor, the antipsychotic or antidepressant being present in the medicament in a therapeutically effective amount for the antipsychotic or antidepressant effect sought, and the antagonist and/or inverse agonist of the histamine $H_3$ receptor being present in a therapeutically effective amount for ensuring at least one of the following three effects: suppression or at least limitation of the undesirable effect of weight gain, suppression or limitation of the undesirable effect on alertness, increase in the procognitive effect of the treatment.

The invention can be applied in particular to antipsychotics or antidepressants and, more generally, psychotropic agents, having an undesirable effect of a gain in body weight and/or sedation due principally to a histamine ($H_1$) antagonistic effect.

There are preferred as the antipsychotic or antidepressant (A) in the medicaments according to the invention, antipsychotic agents, such as olanzapine, risperidone, clozapine, quetiapine, or antidepressants, such as mirtazapine or paroxetine, amitriptyline, aripiprazole and carbamazepine; preferably olanzapine.

Preferably, the doses of antipsychotic and/or antidepressant are equal to or similar to those of the corresponding antipsychotic or antidepressant drugs already in use.

According to the present invention, it is possible, in particular, to use an imidazole derivative as the antagonist/inverse agonist (B) of histamine at the $H_3$ receptor, numerous derivatives having been described, for example, in the documents listed below.

However, an antagonist or an agonist described in the application PCT/EP99/05744 is preferably used. The content of that application and of its U.S. national phase Ser. No. 09/622,199, and divisional application Ser. No. 10/856,838 is incorporated herein by reference.

Thus, in a preferred embodiment, compound (B) is an antagonist or a partial or inverse agonist of histamine at the $H_3$ receptor having the formula (I)

in which

W is a residue which, when it is attached to an imidazole ring in the 4 (5)-position, confers on such a molecule an antagonist or inverse agonist activity at the histamine $H_3$ receptor, such residues W being amply described in the literature and especially in the various documents listed hereinafter, $R^1$ and $R^2$, which may be identical or different, each represent, independently, a C1-C6 alkyl or a cycloalkyl, or, taken together with the nitrogen atom to which they are attached, a saturated nitrogen-containing ring i)

in which m is from 2 to 8 or a non-aromatic unsaturated nitrogen-containing ring ii)

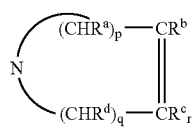

in which p and q independently are from 0 to 3 and r is from 0 to 4, provided that p and q are not simultaneously 0 and that $2 \leq p+q+r \leq 8$, $R^{a-d}$ being, independently, a hydrogen atom or a C1-C6 alkyl group, a cycloalkyl or an alkoxycarbonyl or a morpholino group or an N-substituted piperazino group

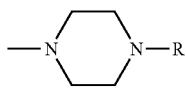

R being a C1-C6 alkyl group, cycloalkyl, alkoxycarbonyl, aryl, arylalkyl, alkanoyl or an aroyl group.

Of those compounds, preference is given to those corresponding to the general formula

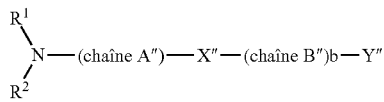 (II)

in which:

i) $R^1$ and $R^2$ are as defined in formula (I)

ii) the chain A" is selected from the linear or branched, saturated or unsaturated hydrocarbon chains containing from 1 to 6 carbon atoms, the saturated hydrocarbon chain optionally being interrupted by a hetero atom which may be a sulphur atom, iii) X" is selected from the oxygen and sulphur atoms, —NH—, —NHCO—, —N(alkyl)CO—, —NHCONH, —NH—CS—NH—, —NHCS—, —O—CO—, —CO—O—, —OCONH—, —OCON(alkyl)-, —OCON(alkene), —OCONH—CO—, —CONH—, —CON(alkyl)-, —SO—, —CO—, —CHOH—, —N(saturated or unsaturated alkyl), —S—C(=NY")—N—Y"—, in which the Y"s may be identical or different, and —NR‴C(=NR'‴)—NR'‴, in which R‴ and R'‴ denote a hydrogen atom or a C1-C6 alkyl radical and R"‴ denotes a hydrogen atom or another powerful electronegative group which may be selected from a cyano or $COY_1$" group, $Y_1$" denoting an alkoxy group;

iv) the chain B" is selected from an aryl, arylalkyl, arylalkanoyl group; a linear alkylene chain —(CH$_2$)$_n$—, n being from 1 to 5, or a branched alkylene chain containing from 2 to 8 carbon atoms, the alkylene chain optionally being interrupted by one or more oxygen or sulphur atoms; and a —(CH$_2$)$_{n''}$—O— or —(CH$_2$)$_{n''}$—S— group in which n‴ is 1 or 2; and v) Y" is selected from a linear or branched alkyl group containing from 1 to 8 carbon atoms; a cycloalkyl containing from 3 to 6 carbon atoms; a bicycloalkyl group; a cycloalkenyl group; an aryl group optionally substituted by a phenyl group; a heterocyclic radical having 5 or 6 elements containing one or two hetero atoms selected from nitrogen and sulphur, the heterocyclic radical optionally being substituted; and a bicyclic radical resulting from the fusion of a benzene ring to a heterocycle as defined above;

or in which ii') the chain A" is selected from a saturated or unsaturated, linear or branched alkylene group —(CH$_2$)$_{n''}$— in which n" is an integer from 1 to 8; a linear or branched alkenylene group comprising from 1 to 8 carbon atoms; and a linear or branched alkynylene group comprising from 1 to 4 carbon atoms;

iii') the group X" is selected from —OCONH—, OCON(alkyl)-, —OCON(alkene)-, —OCO—, —OCOSNH—, —CH$_2$—, —O—, —OCH$_2$CO—, —S—, —CO—, —CS—, an amine or a saturated or unsaturated alkyl;

iv') the chain B" is selected from the saturated or unsaturated, linear or branched alkylenes comprising from 1 to 8 carbon atoms; and —(CH$_2$)$_{n''}$(hetero atom)—where the hetero atom is preferably an oxygen or sulphur atom; n" being an integer from 1 to 5; and v') the group Y" represents a phenyl group which is unsubstituted or mono- or polysubstituted by one or more identical or different substituents selected from the halogen atoms, OCF$_3$, CHO, CF$_3$, SO$_2$N(alkyl)$_2$ such as SO$_2$N(CH$_3$)$_2$, NO$_2$, S(aryl), SCH$_2$(phenyl), a linear or branched alkene, a linear or branched alkyne optionally substituted by a trialkylsilyl radical, —O(alkyl)-, —O(aryl), —CH$_2$CN, a ketone, an aldehyde, a sulphone, an acetal, an alcohol, a C$_1$-C$_6$ alkyl, —CH=CH—CHO, —C(alkyl)=N—OH, —C(alkyl)=N—O(alkyl) and other ketone derivatives, —CH=NOH, —CH=NO(alkyl) and other aldehyde derivatives, —C(alkyl)=NH—CONH$_2$, and O-phenyl or the group —OCH$_2$(phenyl), —C(cycloalkyl)=NOH, —C(cycloalkyl)=N—O(alkyl); an optionally substituted heterocycle, a cycloalkyl; a bicyclic group and preferably a norbornyl group; a phenyl ring fused to a heterocycle comprising a nitrogen hetero atom or to a carbocycle or to a heterocycle having a ketone function; a linear or branched alkyl comprising from 1 to 8 carbon atoms; a linear or branched alkyne comprising from 1 to 8 carbon atoms and especially from 1 to 5 carbon atoms; a linear or branched alkyl mono- or polysubstituted by phenyl groups which are unsubstituted or mono- or polysubstituted; a phenyl alkyl ketone in which the alkyl group is linear or branched or cyclic; a substituted or unsubstituted benzophenone; a substituted or unsubstituted, linear, branched or cyclic phenyl alcohol; a linear or branched alkene; a piperidyl group; a phenyl cycloalkyl group; a polycyclic group, especially a fluorenyl group, a naphthyl or polyhydronaphthyl group or an indanyl group; a phenol group; a ketone or a ketone derivative; a diphenyl group, a phenoxyphenyl group; a benzyloxyphenyl group, —CN, -alkyl, -aryl, -alkylCOalkyl, —COOalkyl, —COalkyl, —COaryl, —COaralkyl, —COcycloalkyl, —OH, -alkyl(OH), -alkyl(Oalkyl), —NHCOalkyl, —NH2.

Preferably, in formula (I) or (II), R1 and R2, taken together with the nitrogen atom to which they are attached, form a saturated nitrogen-containing ring i)

in which m is from 2 to 8, preferably 5; and $R^{a-b}$ represent, independently, a hydrogen atom or a C1-C6 alkyl group, preferably a hydrogen atom.

Preferably, in formula (II), the chain A" is selected from the linear or branched, saturated or unsaturated hydrocarbon chains containing from 1 to 6 carbon atoms, preferably the C1-C6 alkyl chains.

Preferably, in formula (II), X" is —O—.

Preferably, in formula (II), B" is selected from an aryl group, a linear alkylene chain —$(CH_2)_n$—, n being from 1 to 5, or a branched alkylene chain containing from 2 to 8 carbon atoms, the alkylene chain optionally being interrupted by one or more oxygen or sulphur atoms; preferably a linear alkylene chain —$(CH_2)_n$—, n being from 1 to 5.

Preferably, in the general formula (II), Y" represents a phenyl group which is unsubstituted or mono- or polysubstituted by one or more identical or different substituents selected from the halogen atoms, $OCF_3$, —CN, -alkyl, -aryl, -alkylCOalkyl, —COOalkyl, —COalkyl, —COaryl, —COaralkyl, —COcycloalkyl, —OH, -alkyl(OH), -alkyl(Oalkyl), —Oaryl, —NHCOalkyl, -Oalkyl, —C(alkyl)=N—OH, —C(alkyl)=N—O(alkyl), —NO2, —NH2, CHO, $CF_3$, $SO_2N(alkyl)_2$ such as $SO_2N(CH_3)_2$, or a phenyl ring fused to a heterocycle comprising a nitrogen hetero atom or to a carbocycle, the fused ring optionally being substituted by the above-mentioned substituents; preferably, Y" represents a phenyl group optionally substituted by a halogen atom.

Of the compounds of formula (II), preference is given to those of formula (IIa)

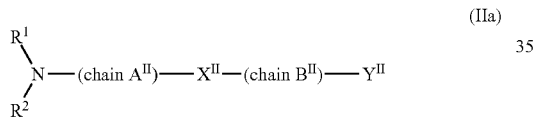

(IIa)

in which:

$R^1$ et $R^2$, which may be identical or different, each represent independently a saturated nitrogen-containing ring i)

in which m is from 2 to 8, $R^{a-b}$ being selected independently from a hydrogen atom or a C1-C4 alkyl radical, and ii) the chain $A^{II}$ is selected from a linear alkyl group —$(CH_2)_{nII}$— in which $n_{II}$ is 3;

iii) the group X" is —O—;

iv) the chain $B^{II}$ is a linear alkyl group comprising 3 carbon atoms; and v) the group $Y^{II}$ represents a phenyl group which is unsubstituted or mono- or polysubstituted by one or more identical or different substituents selected from the halogen atoms, $OCF_3$, CHO, $CF_3$, $SO_2N(alkyl)_2$ such as $SO_2N(CH_3)_2$, $NO_2$, S(aryl), $SCH_2$(phenyl), -alkylCOalkyl, —COOalkyl, —COalkyl, —COaryl, —COaralkyl, —COcycloalkyl, -alkyl(OH), -alkyl(Oalkyl), —Oaryl, —NHCOalkyl, —Oalkyl, —C(alkyl)=N—OH, —C(alkyl)=N—O(alkyl), —NO2, —NH2, a linear or branched alkene, a linear or branched alkyne optionally substituted by a trialkylsilyl radical, —O(alkyl), —O(aryl), —$CH_2CN$, a ketone, an aldehyde, a sulphone, an acetal, an alcohol, a C1-C4 alkyl, —CH=CH—CHO, —C(alkyl)=N—OH, —C(alkyl)=N—O(alkyl) and other ketone derivatives, —CH=NOH, —CH=NO(alkyl), and other aldehyde derivatives, —C(alkyl)=NH—NH—$CONH_2$, O-phenyl or —$OCH_2$(phenyl), —C(cycloalkyl)=NOH, —C(cycloalkyl)=N—O(alkyl).

Preferably, in formula (IIa), m is 4 or 5.

Preferably, in formula (IIa), —$NR^1R^2$ is selected from the piperidyl or pyrrolidinyl group.

Preferably, in formula (IIa), $R^a$ is a hydrogen atom.

Preferably, in formula (IIa), the saturated nitrogen-containing ring is mono- or di-substituted.

Preferably, in formula (IIa), the saturated nitrogen-containing ring is mono-substituted by an alkyl group, preferably a methyl group.

Preferably, in formula (IIa), the substituents(s) is(are) in the beta position with respect to the nitrogen atom.

Preferably, in formula (IIa), $Y^{II}$ represents a phenyl group which is at least monosubstituted by a ketone group, which may include a ketone having a C1-C8 aliphatic chain, and which is optionally substituted by a hydroxyl group, a cycloalkyl ketone, aryl alkyl ketone or aryl alkenyl ketone group, in which the aryl group is optionally substituted, or a heteroaryl ketone group.

Preferably, in formula (IIa), $Y^{II}$ is a phenyl which is at least mono-substituted by —CHO, a ketone, an aldehyde, —CH=CH—CHO, —C(alkyl)=N—OH, —C(alkyl)=N—O(alkyl) and other ketone derivatives, —CH=N—OH, —CH=NO(alkyl) and other aldehyde derivatives, —C(cycloalkyl)=NOH, —C(cycloalkyl)=N—O(alkyl).

Preferably, the compound of formula (IIa) is selected from:

3-Phenylpropyl 3-piperidinopropyl ether
3-(4-Chlorophenyl)propyl 3-piperidinopropyl ether
3-Phenylpropyl 3-(4-methylpiperidino)propyl ether
3-Phenylpropyl 3-(3,5-cis-dimethylpiperidino)propyl ether
3-Phenylpropyl 3-(3,5-trans-dimethylpiperidino)propyl ether
3-Phenylpropyl 3-(3-methylpiperidino)propyl ether
3-Phenylpropyl 3-pyrrolidinopropyl ether
3-(4-Chlorophenyl)propyl 3-(4-methylpiperidino)propyl ether
3-(4-Chlorophenyl) propyl 3-(3,5-cis-dimethyl piperidino)propyl ether
3-(4-Chlorophenyl) propyl 3-(3,5-trans-dimethyl piperidino)propyl ether.

Even more preferably, the compound of formula (IIa) is 3-(4-chlorophenyl)propyl-3-piperidinopropyl ether, or its pharmaceutically acceptable salts, hydrates, or hydrated salts, or the polymorphic crystalline structures of those compounds or their optical isomers, racemates, diastereoisomers or enantiomers.

Preferably, the compounds of formula (IIa) are in the form of pharmaceutically acceptable salts and those salts are selected from the chlorohydrate, the bromohydrate, the hydrogen maleate and the hydrogen oxalate.

The above-indicated formulae and definitions of compounds according to the invention cover the compounds in free form as well as their pharmaceutically acceptable salts, hydrates, or hydrated salts, or the polymorphic crystalline structures of those compounds or their optical isomers, racemates, diastereoisomers or enantiomers.

More precisely, the compounds may also be present in the form of their pharmaceutically acceptable salts, hydrates or hydrated salts or their polymorphic crystalline structures or their optical isomers, racemates, diastereoisomers or enantiomers, having the function of an antagonistic ligand at the histamine $H_3$ receptors.

The preferred salts include the chlorohydrate, the bromohydrate, the hydrogen maleate or the hydrogen oxalate.

A particularly preferred compound is the compound known as BF2649, namely 3-(4-chlorophenyl)propyl-3-piperidinopropyl ether, which is also called 1-{3-[3-(4-chlorophenyl)propoxy]propyl}piperidine.

Other antagonists of the $H_3$ receptor and also inverse agonists are described in the following documents: EP 197 840, EP 494 010, WO93/14070, WO96/29315, U.S. Pat. No. 6,248,765, WO92/15567, WO93/20061, WO93/20062, WO95/11894, U.S. Pat. No. 5,486,526, WO93/12107, WO93/12108, WO95/14007, WO95/06037, WO97/29092, EP 680960, WO96/38141, WO96/38142, WO96/40126, Plazzi et al., *Eur. J. Med. Chem.* 1995, 30, 881, Clitherow et al., *Bioorg. & Med. Chem. Lett.* 6(7), 883-838 (1996), Wolin et al., *Bioorg. & Med. Chem. Lett.;* 8, 2157 (1998), also WO 03/11856 A1 20030213; WO 03/24928 A2 20030327; WO 03/24929 A1 20030327; WO 02/79168 A1 20021010; WO 02/24695 A2 20020328; WO 02/12224 A2 20020214; WO 02/32893 A2 20020425; WO 02/12190 A2 20020214; US 2002183309 A1 20021205; WO 02/76925 A2 20021003; WO 02/12214 A2 20020214; WO 02/13821 A1 20020221; US 2002111340 A1 20020815; WO 02/06223 A1 20020124; WO 01/81317 A1 20012201; WO 01/74810 A2 20011011; WO 01/74813 A2 20011011; WO 01/68652 A1 20010920; WO 01/68651 A1 20010920; WO 01/74815 A2 20011011; WO 01/74814 A1 20011011; WO 01/66534 A2 20010913; U.S. Pat. No. 6,166,060 20001226; U.S. Pat. No. 6,100,279 20000808; U.S. Pat. No. 6,034,251 A 20000307; EP 978512 A1 20000209; WO 00/06254 A2 20000210; WO 00/42023 A1 20000720; WO 00/53596 A2 20000914; WO 00/23438 A1 20000427; WO 00/06552 A1 20000210; WO 00/64884 A1 20001102; WO 00/63208 A1 20001026; U.S. Pat. No. 5,932,596 A 19990803; WO 99/05114 A2 19990204; U.S. Pat. No. 6,008,240 A 19991228; WO 99/24421 A1 19990520; WO 99/42458 A1 19990826; WO 99/05141 A1 19990204; U.S. Pat. No. 5,990,317 A 19991123; WO 99/05115 A1 19990204; U.S. Pat. No. 5,869,479 A 19990209; U.S. Pat. No. 5,837,718 A 19981117; U.S. Pat. No. 5,639,775 A 19970617; WO 97/29092 A1 19970814; U.S. Pat. No. 5,463,074 A 19951031; WO 94/17058 A1 19940804; WO 93/12093 A1 19930624; U.S. Pat. No. 5,217,986 A 19930608; WO 91/17146 A1 19911114.

There may be mentioned as individual compounds:
1-(5-phenoxypentyl)-piperidine
1-(5-phenoxypentyl)-pyrrolidine
N-methyl-N-(5-phenoxypentyl)-ethylamine
1-(5-phenoxypentyl)-morpholine
N-(5-phenoxypentyl)-hexamethyleneimine
N-ethyl-N-(5-phenoxypentyl)-propylamine
1-(5-phenoxypentyl)-2-methyl-piperidine
1-(5-phenoxypentyl)-4-propyl-piperidine
1-(5-phenoxypentyl)-4-methyl-piperidine
1-(5-phenoxypentyl)-3-methyl-piperidine
1-acetyl-4-(5-phenoxypentyl)-piperazine
1-(5-phenoxypentyl)-3,5-trans-dimethyl-piperidine
1-(5-phenoxypentyl)-3,5-cis-dimethyl-piperidine
1-(5-phenoxypentyl)-2,6-cis-dimethyl-piperidine
4-carboethoxy-1-(5-phenoxypentyl)-piperidine
3-carboethoxy-1-(5-phenoxypentyl)-piperidine
1-[3-(4-cyclopropylcarbonylphenoxy)propyl]-piperidine
1-[3-(4-acetylphenoxy)-2-R-methylpropyl]piperidine
1-[3-(4-cyanophenoxy)propyl]-4-methylpiperidine
1-[3-(4-cyanophenoxy)propyl]-3-methylpiperidine
1-[3-(4-acetylphenoxy)-2-S-methylpropyl]piperidine
1-{3-[4-(3-oxobutyl)phenoxy]propyl}piperidine
1-[3-(4-cyano-3-fluorophenoxy)propyl]piperidine
1-[3-(4-nitrophenoxy)propyl]-3-methylpiperidine
1-[3-(4-cyanophenoxy)propyl]-2-methylpiperidine
1-[3-(4-nitrophenoxy)propyl]-2-methylpiperidine
1-[3-(4-nitrophenoxy)propyl]-4-methylpiperidine
1-[3-(4-cyanophenoxy)propyl]-2,6-dimethylpiperidine
1-[3-(4-propionylphenoxy)propyl]-3-methylpiperidine
1-[3-(4-cyclobutylcarbonylphenoxy)propyl]piperidine
1-[3-(4-cyclopentylcarbonylphenoxy) propyl]piperidine
1-[3-(4-cyanophenoxy)propyl]-cis-2-methyl-5-ethylpiperidine
1-[3-(4-cyanophenoxy)propyl]-trans-2-methyl-5-ethylpiperidine
1-[3-(4-cyanophenoxy)propyl]-cis-3,5-dimethylpiperidine
1-[3-(4-propionylphenoxy)propyl]-4-methylpiperidine
1-[3-(4-propionylphenoxy)propyl]-2-methylpiperidine
1-{3-[4-(1-hydroxypropyl)phenoxy]propyl}-3-methylpiperidine
1-{3-[4-(1-hydroxypropyl)phenoxy]propyl}-4-methylpiperidine
1-[3-(4-propionylphenoxy)propyl]-2-methylpiperidine
1-[3-(4-propionylphenoxy)propyl]-4-methylpiperidine methoxime
1-[3-(4-cyanophenoxy)propyl]-trans-3,5-dimethylpiperidine
1-[3-(4-cyclopropylcarbonylphenoxy) propyl]-trans-3,5-dimethyl piperidine
1-[3-(4-cyclopropylcarbonylphenoxy) propyl]-cis-3,5-dimethyl piperidine
1-[3-(4-carbomethoxyphenoxy)propyl]piperidine
1-[3-(4-propenylphenoxy)propyl]-2-methyl piperidine
1-[3-(4-propionylphenoxy)propyl]-2-methylpiperidine
1-{3-[4-(1-ethoxypropyl)phenoxy]propyl}-2-methyl piperidine
1-[3-(4-propionylphenoxy)propyl]-4-methylpiperidine
1-[3-(4-bromophenoxy)propyl]piperidine
1-[3-(4-nitrophenoxy)propyl]piperidine
1-[3-(4-N,N-dimethylsulfonamidophenoxy) propyl]piperidine
1-[3-(4-isopropylphenoxy)propyl]piperidine
1-[3-(4-sec-butylphenoxy)propyl]piperidine
1-[3-(4-propylphenoxy)propyl]piperidine
1-[3-(4-ethylphenoxy)propyl]piperidine
1-(5-phenoxypentyl)-1,2,3,6-tetrahydropyridine
1-[5-(4-nitrophenoxy)-pentyl]-pyrrolidine
1-[5-(4-chlorophenoxy)-pentyl]-pyrrolidine
1-[5-(4-methoxyphenoxy)-pentyl]-pyrrolidine
1-[5-(4-methylphenoxy)-pentyl]-pyrrolidine
1-[5-(4-cyanophenoxy)-pentyl]-pyrrolidine
1-[5-(2-naphthyloxy)-pentyl]-pyrrolidine
1-[5-(1-naphthyloxy)-pentyl]-pyrrolidine
1-[5-(3-chlorophenoxy)-pentyl]-pyrrolidine
1-[5-(4-phenylphenoxy)-pentyl]-pyrrolidine
1-{5-[2-(5,6,7,8-tetrahydronaphthyl)-oxy]-pentyl}-pyrrolidine
1-[5-(3-phenylphenoxy)-pentyl]-pyrrolidine
1-(5-phenoxypentyl)-2,5-dihydropyrrole
1-{5-[1-(5,6,7,8-tetrahydronaphthyl)-oxy]-pentyl}-pyrrolidine
1-(4-phenoxybutyl)-pyrrolidine
1-(6-phenoxyhexyl)-pyrrolidine
1-(5-phenylthiopentyl)-pyrrolidine
1-(4-phenylthiobutyl)-pyrrolidine 1-(3-phenoxypropyl)-pyrrolidine
1-[5-(3-nitrophenoxy)-pentyl]-pyrrolidine
1-[5-(4-fluorophenoxy)-pentyl]-pyrrolidine
1-[5-(4-nitrophenoxy)-pentyl]-3-methyl-piperidine
1-[5-(4-acetylphenoxy)-pentyl]-pyrrolidine
1-[5-(4-aminophenoxy)-pentyl]-pyrrolidine
1-[5-(3-cyanophenoxy)-pentyl]-pyrrolidine
N-[3-(4-nitrophenoxy)-propyl]-diethylamine
N-[3-(4-cyanophenoxy)-propyl]-diethylamine
1-[5-(4-benzoylphenoxy)-pentyl]-pyrrolidine
1-{5-[4-(phenylacetyl)-phenoxy]-pentyl}-pyrrolidine
N-[3-(4-acetylphenoxy)-propyl]-diethylamine
1-[5-(4-acetamidophenoxy)-pentyl]-pyrrolidine
1-[5-(4-phenoxyphenoxy)-pentyl]-pyrrolidine
1-[5-(4-N-benzamidophenoxy)-pentyl]-pyrrolidine
1-{5-[4-(1-hydroxyethyl)-phenoxy]-pentyl}-pyrrolidine
1-[5-(4-cyanophenoxy)-pentyl]-diethylamine
1-[5-(4-cyanophenoxy)-pentyl]-piperidine
N-[5-(4-cyanophenoxy)-pentyl]-dimethylamine
N-[2-(4-cyanophenoxy)-ethyl]-diethylamine
N-[3-(4-cyanophenoxy)-propyl]-dimethylamine
N-[4-(4-cyanophenoxy)-butyl]-diethylamine
N-[5-(4-cyanophenoxy)-pentyl]-dipropylamine
1-[3-(4-cyanophenoxy)-propyl]-pyrrolidine
1-[3-(4-cyanophenoxy)-propyl]-piperidine
N-[3-(4-cyanophenoxy)-propyl]-hexamethyleneimine
N-[6-(4-cyanophenoxy)-hexyl]-diethylamine
N-[3-(4-cyanophenoxy)-propyl]-dipropylamine
N-3-[4-(1-hydroxyethyl)-phenoxy]-propyl-diethylamine
4-(3-diethylaminopropoxy)-acetophenone-oxime
1-[3-(4-acetylphenoxy)-propyl]-piperidine
1-[3-(4-acetylphenoxy)-propyl]-3-methyl-piperidine
1-[3-(4-acetylphenoxy)-propyl]-3,5-trans-dimethyl-piperidine
1-[3-(4-acetylphenoxy)-propyl]-4-methyl-piperidine
1-[3-(4-propionylphenoxy)-propyl]-piperidine
1-[3-(4-acetylphenoxy)-propyl]-3,5-cis-dimethyl-piperidine
1-[3-(4-formylphenoxy)-propyl]-piperidine
1-[3-(4-isobutyrylphenoxy)-propyl]-piperidine
N-[3-(4-propionylphenoxy)-propyl]-diethylamine
1-[3-(4-butyrylphenoxy)-propyl]-piperidine
1-[3-(4-acetylphenoxy)-propyl]-1,2,3,6-tetrahydropyridine
α-(4-Acetylphenoxy)-α'-(4-methylpiperidino)p-xylol
α-(4-Acetylphenoxy)-α'-(3,5-cis-dimethylpiperidino)p-xylol
α-(4-Acetylphenoxy)-α'-(3,5-trans-dimethylpiperidino)p-xylol
α-(4-Acetylphenoxy)-α'-(2-methylpyrrolidino)p-xylol
α-(4-Cyclopropylcarbonylphenoxy)-α'-piperidino-p-xylol
α-(4-Cyclopropylcarbonylphenoxy)-α'-(4-methylpiperidino)p-xylol
α-(4-Cyclopropylcarbonylphenoxy)-α'-pyrrolidino-p-xylol
3-Phenylpropyl 3-(4-methylpiperidino)propyl ether
3-Phenylpropyl 3-(3,5-cis-dimethylpiperidino)propyl ether
3-Phenylpropyl 3-(3,5-trans-dimethylpiperidino)propyl ether
3-Phenylpropyl 3-(3-methylpiperidino)propyl ether
3-Phenylpropyl 3-pyrrolidinopropyl ether
3-(4-Chlorophenyl)propyl 3-(4-methylpiperidino)propyl ether
3-(4-Chlorophenyl)propyl 3-(3,5-cis-dimethylpiperidino)propyl ether
3-(4-Chlorophenyl)propyl 3-(3,5-trans-dimethylpiperidino)propyl ether
4-(6-Piperidinohexylamino)quinoline
2-Methyl 4-(3-piperidinopropylamino)quinoline
2-Methyl 4-(6-piperidinohexylamino)quinoline
7-Chloro-4-(3-piperidinopropylamino)quinoline
7-Chloro-4-(4-piperidinobutylamino)quinoline
7-Chloro-4-(8-piperidinooctylamino)quinoline
7-Chloro-4-(10-piperidinodecylamino)quinoline
7-Chloro-4-(12-piperidinododecylamino)quinoline
7-Chloro-4-(4-(3-piperidinopropoxy)phenylamino)quinoline
7-Chloro-4-(2-(4-(3-piperidinopropoxy)phenyl)ethylamino)quinoline
4-(6-Piperidinohexanoyl)phenyl 3-piperidinopropyl ether
5-Nitro-2-(5-piperidinopentylamino)pyridine
3-Nitro-2-(6-piperidinopentylamino)pyridine
5-Amino-2-(6-piperidinopentylamino)pyridine
2-(6-Piperidinohexylamino)quinoline
N-(4-Chlorobenzyl)-N'-cyclohexyl-3-piperidinopropyl isothiourea
2-(6-Piperidinohexylamino)benzothiazole
10-Piperidinodecylamine
3-Phenylpropyl 3-(N,N-diethylamino)propyl ether
N-(3-(N,N-Diethylamino)propyl)N'-phenylurea
N-Cyclohexylmethyl-N'-(3-piperidinopropyl)guanidine
N-(4-Bromobenzyl)-N'-(4-piperidinobutyl)sulphamide
3-Chloro-N-(4-piperidinobutyl)-N-methyl-benzene sulphonamide
N-(4-Chlorobenzyl)-2-(4-piperidinomethyl) phenyl) ethane amidine
1-(5-Cyclohexylpentanoyl)-1,4-bipiperidine
cis-1-(6-Cyclohexyl-3-hexen-1-yl)piperidine
trans-1-(6-Cyclohexyl-3-hexen-1-yl)piperidine
1-(2-(5,5-Dimethyl-1-hexin-1-yl)cyclopropyl)piperidine
3,3-Dimethylbutyl 3-piperidinopropyl ether
3-Phenylpropyl 3-piperidinopropyl ether
3-(4-Chlorophenyl)propyl 3-piperidinopropyl ether
2-Benzothiazolyl 3-piperidinopropyl ether
3-Phenylpropyl 3-(4-methylpiperidino)propyl ether
3-Phenylpropyl 3-(3,5-cis-dimethylpiperidino)propyl ether
3-Phenylpropyl 3-(3,5-trans-dimethylpiperidino)propyl ether
3-Phenylpropyl 3-(3-methylpiperidino)propyl ether
3-Phenylpropyl 3-pyrrolidinopropyl ether
3-(4-Chlorophenyl)propyl 3-(4-methylpiperidino)propyl ether
3-(4-Chloro phenyl) propyl 3-(3,5-cis-dimethyl piperidino)propyl ether
3-(4-Chloro phenyl) propyl 3-(3,5-trans-dimethyl piperidino)propyl e1her
3-Phenylpropyl 3-(N,N-diethylamino)propyl ether
N-Phenyl-3-piperidinopropyl carbamate
N-Pentyl-3-piperidinopropyl carbamate
(S)-(+)-N-[2-(3,3-Dimethyl)butyl]-3-piperidinopropyl carbamate
3-Cyclopentyl-N-(3-(1-pyrrolidinyl)propyl)propanamide
N-Cyclohexyl-N'-(1-pyrrolidinyl-3-propyl)urea
2-((2-Piperidinoethyl)amino)benzothiazole
5-Piperidinopentylamine
2-Nitro-5-(6-piperidinohexyl)pyridine
3-Nitro-2-(6-piperidinohexylamino)pyridine
2-(6-Piperidinohexylamino)pyrimidine
N-(6-Phenylhexyl)piperidine
N-(3-(N,N-Diethylamino)propyl)N'-phenylurea
N-Cyclohexylmethyl-N'-(3-piperidinopropyl)guanidine 3-(3,4-Dimethoxyphenyl)propyl 3-piperidinopropyl ether
3-(4-Fluorophenyl)propyl 3-pyrrolidinopropyl ether
3-(4-Hydroxy-3-methoxyphenyl)propyl 3-piperidinopropyl ether
3-(3-Hydroxy-4-methoxyphenyl)propyl 3-piperidinopropyl ether
3-(4-Fluoro-3-methoxyphenyl)propyl 3-piperidinopropyl ether
3-(4-Fluoro-3-methoxyphenyl)propyl 3-pyrrolidinopropyl ether
1-[3-(4-butylphenoxy)propyl]piperidine
1-[3-(4-phenylphenoxy)propyl]piperidine
1-{3-[4-(3-oxobutyl)phenoxy]propyl}-3,5-trans-d1methyl-piperidine
1-{3-[4-(3-oxobutyl)phenoxy]propyl}-3,5-cis-dimethyl-piperidine
1-[3-(4-butylphenoxy)propyl]-3,5-trans-dimethyl-piperidine
1-[3-(4-butylphenoxy)propyl]-3,5-cis-dimethyl-piperidine
1-[3-(4-phenylphenoxy)propyl]-3,5-trans-dimethyl-piperidine
1-[3-(4-phenylphenoxy)propyl]-3,5-cis-dimethyl-piperidine or its pharmaceutically acceptable salts, hydrates, or hydrated salts, or the polymorphic crystalline structures of those compounds or their optical isomers, racemates, diastereoisomers or enantiomers.

There may be especially mentioned as individual compounds:

3-phenylpropyl 3-piperidinopropyl ether;
1-[5-(4-acetamidophenoxy)-pentyl]-pyrrolidine;
1-(3-[4-oxobutyl)phenoxyl]propyl)piperidine;
1-(3-[4-(1-hydroxypropyl)phenoxy]propyl)-3-methylpiperidine
1-3-[4-(1-hydroxypropyl)phenoxy]propyl)-4-methylpiperidine;
1-[3-(4-cyanophenoxy)-propyl]-piperidine;
N-[3-(4-cyanophenoxy)-propyl]-hexamethyleneimine;
1-[3-(4-acetylphenoxy)-propyl]-3-methyl-piperidine;
1-(3-[4-(1-ethoxypropyl)phenoxy]propyl)-2-methylpiperidine oxime
1-[3-(4-bromophenoxy)propyl]piperidine;
1-[3-(4-isopropylphenoxy)propyl]piperidine
1-[3-(4-sec-butylphenoxy)propyl]piperidine
1-[3-(4-propylphenoxy)propyl]piperidine;
1-[3-(4-ethylphenoxy)propyl]piperidine.

Those compounds are described in the application PCT/EP99/05744 (WO00/06254). They can be prepared by applying or adapting the methods described in that application, or by any other method within the competence of the person skilled in the art.

In particular, the following products were prepared in accordance with those methods and have the following features:

3-(3,4-Dimethoxyphenyl)propyl 3-piperidinopropyl ether (oxalate salt): M.P.=111° C.
3-(4-Fluorophenyl)propyl 3-pyrrolidinopropyl ether (oxalate salt): M.P.=106° C.
3-(4-Hydroxy-3-methoxyphenyl)propyl 3-piperidinopropyl ether (oxalate salt): M.P.=110-111° C.
3-(3-Hydroxy-4-methoxyphenyl)propyl 3-piperidinopropyl ether (oxalate salt): M.P.=101-103° C.
3-(4-Fluoro-3-methoxyphenyl)propyl 3-piperidinopropyl ether (oxalate salt): M.P.=125-126° C.
3-(4-Fluoro-3-methoxyphenyl)propyl 3-pyrrolidinopropyl ether (oxalate salt): M.P.=87-88° C.
1-{3-[4-(3-oxobutyl)phenoxy]propyl}-3,5-cis-dimethyl-piperidine (oxalate salt): M.P.=114° C.
1-{3-[4-(3-oxobutyl)phenoxy]propyl}-3,5-trans-dimethyl-piperidine (oxalate salt): M.P.=120° C.

The proportions of compound (A) with respect to compound (B) are preferably from 5 to 100 mg, more preferably from 5 to 80 mg of compound (B) for 0.5 to 50 mg of compound (A).

For compound (A), it is preferable to use, in terms of posology, dosages that are identical or similar to the dosages normally used for antipsychotic or antidepressant treatments.

However, in one particular embodiment, and bearing in mind an anti-psychotic or antidepressant effect belonging to compound (B), the dose of compound (A) can be reduced, for example to 50-90%, of the usual dose.

For compound (B), the dose used may correspond to a normal dose such as taught in the above-mentioned patent application or 5-80 mg, for example 20-50 mg of compound BF 2649.

However, in an improved embodiment, that dose may be reduced, being preferably equal to at least 10 to 15% of the normal dose, for example 50% of the normal dose.

The medicament according to the invention can be administered by any administration route suitable for antipsychotic administration or as an antidepressant. Preferably, oral administration is provided for.

Consequently, the medicament may be made up in the form of tablets, capsules, powder or any form for a solid oral preparation or in any form of drinkable preparation. The formulation may be combined with a pharmaceutically acceptable vehicle, for example, for the preparation of tablets or capsules or for a drinkable preparation, such as the vehicles which are used in an entirely conventional manner in the pharmacopoeia and which, in particular, are already used for the neuroleptics described in the invention.

In order to determine the neuroleptics or other antipsychotic and/or antidepressant drugs suitable for use in the medicaments according to the invention, a search can be conducted by in vitro, and optionally in vivo, tests for the psychotropic agents blocking the $H_1$ receptors. Such tests are described, for example, in Quach et al., *Eur. J. Pharmacol.*, 1979, 60, 391.

Thus, of those psychotropic drugs, carbamazepine may be described in addition to the antipsychotics and antidepressants described above.

The invention relates also to the use of an antagonist and/or inverse agonist of the histamine $H_3$ receptor, that is to say, of a compound (B) such as described above, for the preparation of a medicament which is to be administered to complement psychiatric treatment by an antipsychotic or an antidepressant in order to prevent or correct the undesirable effects of such treatment on weight gain and/or alertness which are caused or could be caused by that treatment.

According to a further preferred aspect, the undesirable effect is in particular epilepsy and/or convulsions. Epilepsy and/or convulsions have been observed in particular as an effect induced by olanzapine, or risperidone, clozapine, mirtazapine. According to a further preferred aspect, the present invention therefore relates to the use of an antagonist and/or inverse agonist of the histamine $H_3$ receptor, that is to say, of a compound (B) such as described above, for the preparation of a medicament which is to be administered to complement psychiatric treatment by an antipsychotic or an antidepressant in order to prevent or correct epilepsy and/or convulsions.

The invention relates also to the use of such a compound for the preparation of a medicament which is to be administered to complement treatment by an antipsychotic or antidepressant in order to potentiate the therapeutic effects of the treatment on the cognitive sphere.

The invention relates also to the use of a compound (A) and of a compound (B) such as defined hereinbefore for the preparation of a medicament for preventing and/or treating a pathology selected from: schizophrenia, depression, psychosis, mental disorders, mania, bipolar affective disorders.

The uses according to the invention may include the manufacture of a medicament comprising, simultaneously, compound (A) and compound (B) as defined above.

Those uses may also provide for the manufacture of a set of distinct compositions, one containing compound (A) and the other compound (B), in combination in the same form of presentation.

Finally, the uses according to the invention may include the manufacture of a medicament which is to prevent or correct the undesirable effects in the above-mentioned treatment, or to potentiate the therapeutic effect on the cognitive sphere in such a treatment, in the form of a medicament comprising solely or substantially compound (B) as the active ingredient.

Such a medicament is manufactured preferably in an oral administration form, similar to those described above.

The dosage of such a medicament preferably includes a dose of compound (B) equal to or less than the dose normally recommended for the already-known use of compound (B). Preferably, the dose is between 15 or 20% and up to 100% of that dose. However, it is also possible to provide for doses larger than the dose normally recommended for compound (B).

Finally, the invention relates to a method of preventing or correcting weight gain and, where appropriate, the associated undesirable effects which are caused or may be caused by antipsychotic or antidepressant treatment, in which method a therapeutically effective amount of a compound (B) as defined above is administered to the patient receiving the treatment.

In this method, compound (B) can be administered either in the form of a combination with the antipsychotic or antidepressant compound (A), forming a single medicament, or it may be administered separately, either concomitantly or independently, for example, in a manner staggered over time.

Preferably, the rate of administration of compound (B) is identical or similar to the rate of administration of compound (A).

The therapeutically active amounts used in the method according to the invention are defined above.

Other advantages and features of the invention will emerge on reading the following description which is given by way of non-limiting example.

EXAMPLE 1

Combination of Olanzapine and Compound BF2649

An oral formulation in the form of tablets or capsules or a drinkable preparation comprising from 5 to 80 mg of compound BF2649 and from 3 to 20 mg of olanzapine is prepared.

Such a formulation is administered preferably once daily.

Preferably, the formulation combines from 20 to 60 mg of compound BF2649 with 20 mg of olanzapine for an adult.

EXAMPLE 2

Combination of Risperidone and Compound BF2649

An oral formulation in the form of tablets or capsules or a drinkable preparation comprising from 5 to 60 mg of compound BF2649 and from 0.5 to 10 mg of risperidone is prepared.

Such a formulation is administered preferably once daily.

Preferably, the formulation combines from 20 to 60 mg of compound BF2649 with 10 mg of risperidone for an adult.

EXAMPLE 3

Combination of Aripiprazole and Compound BF2649

An oral formulation in the form of tablets or capsules or a drinkable preparation comprising from 5 to 60 mg of compound BF2649 and from 10 to 30 mg of aripiprazole is prepared.

Such a formulation is administered preferably once daily.

Preferably, the formulation combines from 20 to 60 mg of compound BF2649 with from 10 to 30 mg of aripiprazole for an adult.

Compound BF2649 is combined with clozapine or quetiapine or an antidepressant such as mirtazapine in a similar manner.

EXAMPLE 4

Use of Compound BF2649

In order to prepare a medicament which is to be used to prevent or correct the undesirable effects of antipsychotic or antidepressant treatment, a composition for oral administration is produced, in particular in the form of tablets, capsules or drinkable preparations, comprising a dose of from 20 to 60 mg of compound BF2649.

The invention thus permits the prevention or correction of the weight gain caused by antipsychotics, antidepressants and other psychotropic agents, and also those other undesirable effects by administering simultaneously an antagonist/inverse agonist of the histamine $H_3$ receptor.

Without wishing to be bound by this theory, the present inventors believe that they can explain this unexpected effect by the following factors:

1) the $H_3$ antagonists/inverse agonists increase considerably the release of brain histamine and, as such, protect the $H_1$ receptor from being blocked by numerous psychotropic agents by a competitive process, 2) the $H_3$ antagonists/inverse agonists tend, by themselves, to reduce food intake (Sakata et al. Nutrition, 1997, 5, 403).

2) The action of the $H_3$ antagonists/inverse agonists does not in any way oppose the action of the antipsychotics or antidepressants and might even promote it. For, by themselves, i) they are found to be active on some animal schizophrenia «models» (blockage of the psychomotive activation induced by amphetamine on the NMDA antagonists), ii) they exert a procognitive effect which is sought in the treatment of both schizophrenia and depression.

3) Their stimulating effect which is demonstrated in humans is such as to oppose the undesirable sedative effect of numerous psychotropic agents. It has also been shown that an $H_3$ antagonist/inverse agonist administered to humans brings about an increase in the high-frequency alpha waves, which are known to be associated with cognitive processes, thereby indicating that this medicament can be used to increase the precognitive effect of antipsychotics, which is sought in the psychoses and mental disorders associated therewith.

Those observations have been confirmed by the following experimental results:

EXAMPLE 5

Activity of the Combinations According to the Invention

Animal Data:

Compound BF2649 was administered intraperitoneally at a dose of 5 mg/kg, alone or in combination with 0.15 mg/kg of olanzapine, per os to mice in which hyperlocomotion was induced (by the administration of 0.2 mg/kg of dizocilpine).

The experimental data show that the separate administration of BF2649 or olanzapine has only marginal effects on the hyperlocomotion induced by dizocilpine, while the administration of the 2 compounds in combination completely prevents the hyperlocomotive effect of 0.2 mg/kg of dizocilpine.

Those results establish that the H3 antagonist potentiates the effects of olanzapine on a number of antipsychotic tests.

Human Data:

A group of 6 male volunteers received orally, successively and at one-week intervals: 1) a placebo 2) olanzapine at a dose of 5 mg 3) BF 2649 at a dose of 60 mg 4) a combination of olanzapine and BF 2649 at the doses indicated above.

The subjects were then analyzed for a period of 24 hours with regard to parameters of alertness (quantitative EEG), cognition (various psychometric tests) and satiety (questionnaires for the self-evaluation of feelings of hunger, desire to eat, gastric fullness). In addition, the levels of the two medicaments in the blood was analyzed repeatedly in the course of the nychthemeron.

It was found that olanzapine, when administered alone, brought about deep sedation accompanied by a decrease in the rapid waves of the EEG to the benefit of the slow waves, a profound deterioration in the psychometric tests, in particular in respect of attention, and a very marked increase in feelings of hunger. BF 2649 was observed to have opposite effects on those various symptoms, which are at the root of the secondary effects of the antipsychotic, and, above all, a sometimes total prevention of the effects of olanzapine was observed when BF 2649 was combined therewith. That prevention in the field of satiety was confirmed by a normalization of the secretion of leptin which had been impaired in the subjects by the administration of olanzapine alone.

In addition, the combination was completely tolerated and did not lead to marked modifications in the plasma levels of either of the medicaments.

The particularly spectacular effect in the field of appetite indicates that the combination is such as to prevent the development of weight gain, type 2 diabetes and metabolic syndrome, which often accompany chronic treatment with antipsychotics of the olanzapine type.

The effects on the quantitative EEG indicate that the pre-cognitive effects of the H3 antagonists are maintained in a subject receiving an antipsychotic drug of the olanzapine type and that the proconvulsant effects thereof will be prevented by the combination with an H3 antagonist.

The invention claimed is:

1. A pharmaceutical composition comprising, in a pharmaceutically acceptable vehicle, olanzapine, which, on its own, has an undesirable effect on satiety, alertness and cognition, and 3-(4-chlorophenyl)propyl-3-piperidinopropyl ether (BF2649), or pharmaceutically-acceptable salts thereof, wherein the olanzapine and the 3-(4-chlorophenyl)propyl-3-piperidinopropyl ether or pharmaceutically-acceptable salts thereof are formulated in the pharmaceutical composition as two distinct compositions, or are formulated together to form a single composition, wherein the olanzapine is present in the pharmaceutical composition in a therapeutically effective amount for the antipsychotic or antidepressant effect sought, and wherein the 3-(4-chlorophenyl)propyl-3-piperidinopropyl ether or pharmaceutically-acceptable salts thereof is present in a therapeutically effective amount for ensuring at least one if the following three effects: suppression or limitation of the undesirable effect of olanzapine on satiety, suppression or limitation of the undesirable effect of olanzapine on alertness, suppression or limitation of the undesirable effect of olanzapine on cognition.

2. The pharmaceutical composition according to claim 1, wherein the olanzapine has an undesirable effect on satiety, alertness or cognition due principally to a histamine ($H_1$) antagonistic effect.

3. The pharmaceutical composition according to claim 1, wherein the proportions of olanzapine with respect to 3-(4-chlorophenyl)propyl-3-piperidinopropyl ether or pharmaceutically-acceptable salts thereof are from 5 to 100 mg of 3-(4-chlorophenyl)propyl-3-piperidinopropyl ether or pharmaceutically-acceptable salts thereof for 0.5 to 50 mg of olanzapine.

4. The pharmaceutical composition according to claim 1, suitable for oral administration.

5. The pharmaceutical composition according to claim 4 in the form of tablets, capsules, powder or a drinkable preparation.

6. The pharmaceutical composition according to claim 1, in particular in the form of a tablet, capsule or drinkable preparation combining from 5 to 80 mg of 3-(4-chlorophenyl) propyl-3-piperidinopropyl ether or pharmaceutically-acceptable salts thereof with from 3 to 20 mg of olanzapine.

7. The pharmaceutical composition of claim 1, wherein the pharmaceutically-acceptable salts are selected from the group consisting of chlorohydrate, bromohydrate, hydrogen maleate, and hydrogen oxalate salts.

8. The pharmaceutical composition of claim 7, wherein the pharmaceutically acceptable salts are chlorohydrate salts.

* * * * *